United States Patent [19]

Reiffenrath et al.

[11] Patent Number: 5,454,975

[45] Date of Patent: Oct. 3, 1995

[54] CYANOPHENYLPYRI(MI)DINE DERIVATIVES AND LIQUID-CRYSTALLINE MEDIUM

[75] Inventors: Volker Reiffenrath, Rossdorf; Matthias Bremer, Darmstadt; Michael Junge, Pfungstadt, all of Germany

[73] Assignee: Merck Patent Gesellschaft mit Beschrankter Haftung, Darmstadt, Germany

[21] Appl. No.: 220,991

[22] Filed: Apr. 1, 1994

[30] Foreign Application Priority Data

Apr. 3, 1993 [DE] Germany .................. 43 11 098.3

[51] Int. Cl.⁶ ............... C09K 19/34; C07D 239/02; C07D 211/70
[52] U.S. Cl. ............... 252/299.61; 544/298; 544/335; 546/339
[58] Field of Search ............... 252/299.61; 544/298

[56] References Cited

U.S. PATENT DOCUMENTS

| | | | |
|---|---|---|---|
| 4,609,485 | 9/1986 | Kitano et al. | 252/299.61 |
| 4,621,901 | 11/1986 | Petrzilka et al. | 359/103 |
| 4,640,796 | 2/1987 | Yoshida et al. | 252/299.61 |
| 4,812,258 | 3/1989 | Krause et al. | 252/299.61 |
| 4,883,609 | 11/1989 | Yamada | 252/299.61 |
| 4,886,621 | 12/1989 | Sage et al. | 252/299.61 |
| 5,122,295 | 6/1992 | Weber et al. | 252/299.01 |
| 5,171,469 | 12/1992 | Hittich et al. | 252/299.01 |
| 5,179,101 | 1/1993 | Huynh-Ba et al. | 544/296 |
| 5,204,017 | 4/1993 | Reiffenrath et al. | 252/299.61 |
| 5,227,484 | 7/1993 | Huynh-Ba et al. | 544/242 |
| 5,250,220 | 10/1993 | Wachtler et al. | 252/299.61 |
| 5,310,501 | 5/1994 | Huynh-Ba et al. | 252/299.63 |
| 5,312,563 | 5/1994 | Coates et al. | 252/299.66 |

FOREIGN PATENT DOCUMENTS 160790 2/1985 European Pat. Off. .
317175 11/1988 European Pat. Off. .
2092169 8/1982 United Kingdom .

*Primary Examiner*—Cynthia Harris
*Attorney, Agent, or Firm*—Millen, White, Zelane & Branigan

[57] ABSTRACT

Cyanopyrimidine derivatives of formula I

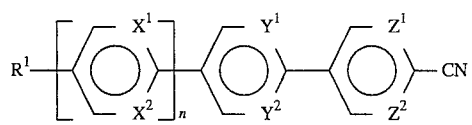

in which $R^1$ is an unsubstituted or at least mono-halogen-substituted alkyl or alkoxy radical having 1 to 15 carbon atoms, where one or more $CH_2$ groups in these radicals may also, in each case independently of one another, be replaced by —CH=CH—, —O—, —S—,

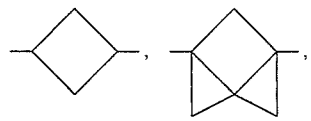

—CO—, —CO—O—, —O—CO— or —O—CO—O— in such a way that oxygen atoms are not linked directly to one another, $X^1$, $Y^1$ and $Z^1$ are each, independently of one another, N or CF, $X^2$, $Y^2$ and $Z^2$ are each, independently of one another, N, CF or CH, and n is 0, 1 or 2, with the proviso that at least one of the groups $X^1$, $Y^1$ and $Z^1$ is N, can be used as components of liquid-crystalline media for electro-optical displays.

6 Claims, No Drawings

CYANOPHENYLPYRI (MI)DINE DERIVATIVES AND LIQUID-CRYSTALLINE MEDIUM

SUMMARY OF THE INVENTION

The invention relates to novel cyanophenylpyri(mi)dine (i.e., cyanophenylpyridine or cyanophenylpyrimidine) derivatives of the formula I

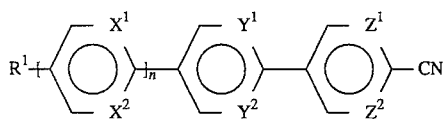

in which

R$^1$ is an unsubstituted or at least mono-halogen-substituted alkyl or alkoxy radical having 1 to 15 carbon atoms, where one or more, preferably one or two, CH$_2$ groups in these radicals may also, in each case independently of one another, be replaced by —CH=CH—, —O—, —S—,

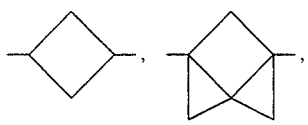

—CO—, —CO—O—, —O—CO— or —O—CO—O— in such a way that oxygen atoms are not linked directly to one another, X$^1$, Y$^1$ and Z$^1$ are each, independently of one another, N or CF, X$^2$, Y$^2$ and Z$^2$ are each, independently of one another, N, CF or CH, and n is 0, 1 or 2, with the proviso that at least one of the groups X$^1$, Y$^1$ and Z$^1$ is N.

The invention furthermore relates to the use of these compounds as components of liquid-crystalline media and to liquid-crystal and electo-optical display elements containing the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable, liquid-crystalline or mesogenic compounds which are suitable as components of liquid-crystalline media and, in particular, simultaneously have relatively low viscosity and extremely high dielectric anisotropy at the same time as good low-temperature behavior.

It has now been found that compounds of the formula I are eminently suitable as components of liquid-crystalline media. In particular, they have unusually high dielectric anisotropy. They can be used to obtain stable liquid-crystalline media having a broad mesophase range and advantageous values for the optical and dielectric anisotropy and very low threshold voltages.

Liquid crystals of the formula

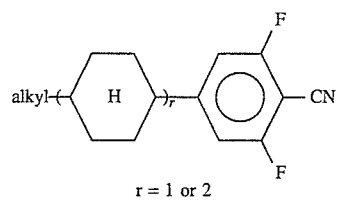

r = 1 or 2 have already been disclosed in DE 32 09 178. EP 0 317 175 discloses pyrimidine derivatives of the formula

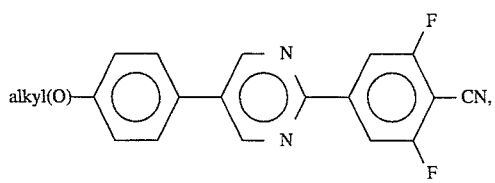

but these are distinguished by fairly high melting points.

EP 0 160 790 describes compounds of the formula

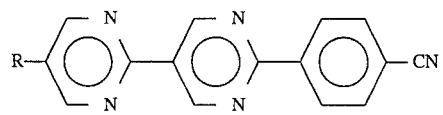

however, their broad smectic phase range means that they are not very suitable as components of nematic media.

In view of the very wide variety of areas of application of such compounds having very high Δε, however, it was desirable to have available further compounds which have properties precisely customized to the particular applications, have significantly higher values for Δε than the compounds disclosed in DE 32 09 178 and have better mesophases, better miscibility with other liquid crystals and higher thermal and UV stability than the compounds disclosed in EP 0 160 790 and EP 0 317 175.

In addition, the provision of the compounds of the formula I very generally suitably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media having improved threshold voltage and containing at least two liquid-crystalline components, characterized in that they contain at least one mesogenic compound which contains a structural unit of the formula II

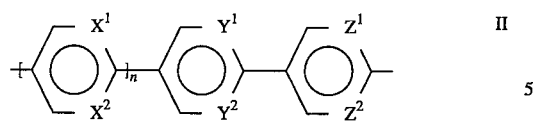 II in which $X^1$, $X^2$, $Y^1$, $Y^2$, $Z^1$ and $Z^2$ are each, independently of one another, CF or N, where the structural unit of the formula II preferably has the empirical formula $C_{16}H_6N_2F_4$, in particular media which contain a compound of the formula I, I1, I2 or I3, and a liquid-crystal display element, in particular an electro-optical display element, which contains media of this type.

Accordingly, the compounds of the formula I cover tricyclic compounds of the subformulae Ia to If

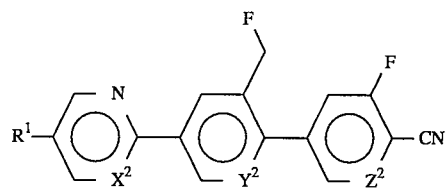 Ia

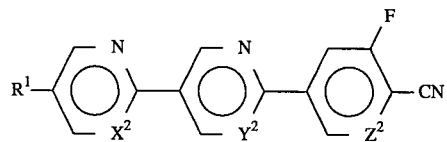 Ib

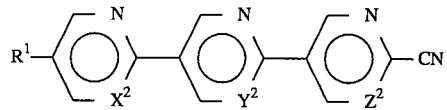 Ic

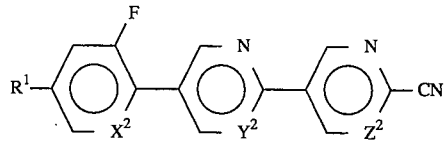 Id

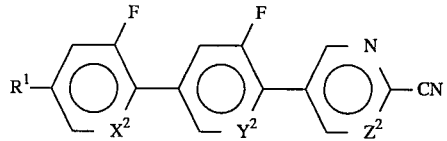 Ie

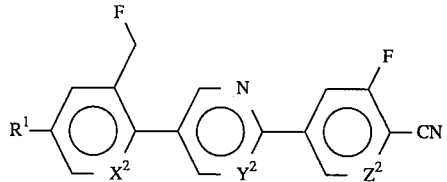 If

In the preferred compounds of the formulae Ia to If, $X^2$, $Y^2$ and $Z^2$ are each, independently of one another, CF or N.

The compounds of the formula I furthermore cover tetracyclic compounds of the subformulae Ig to Iu where the following abbreviations are used:

Py is

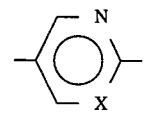

Cl is

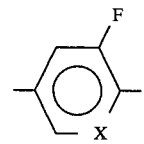

where X is CH, CF or N:

$R^1$—Py—Cl—Cl—Cl—CN Ig
$R^1$—Cl—Py—Cl—Cl—CN Ih
$R^1$—Cl—Cl—Py—Cl—CN Ii
$R^1$—Cl—Cl—Cl—Py—CN Ij
$R^1$—Py—Py—Cl—Cl—CN Ik
$R^1$—Py—Cl—Py—Cl—CN Il
$R^1$—Py—Cl—Cl—Py—CN Im
$R^1$—Cl—Py—Py—Cl—CN In
$R^1$—Cl—Py—Cl—Py—CN Io
$R^1$—Cl—Cl—Py—Py—CN Ip
$R^1$—Py—Py—Py—Cl—CN Ir
$R^1$—Py—Py—Cl—Py—CN Is
$R^1$—Py—Cl—Py—Py—CN It
$R^1$—Cl—Py—Py—Py—CN Iu

Of the compounds of the formulae Ig to In, preference is given to those in which Py is

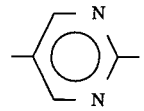

and
Cl is

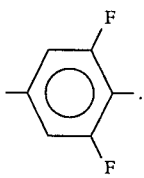

Preferred embodiments are:
a) Cyanophenylpyrimidine derivatives of the formula I in which
 $X^2$, $Y^2$ and $Z^2$ are each, independently of one another, N or CF,
b) Cyanophenylpyrimidine derivatives of the formula I in which the groups
 $X^1$ and $X^2$ are N or CF,
 $Y^1$ and $Y^2$ are N or CF, and
 $Z^1$ and $Z^2$ are N or CF,
d) Cyanophenylpyrimidine derivatives of the formula I1

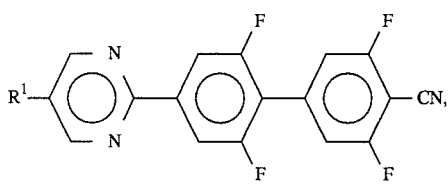

e) Cyanophenylpyrimidine derivatives of the formula I2

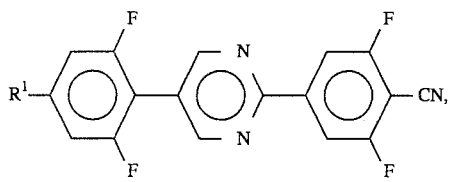

f) Cyanopyrimidine derivatives of the formula I3

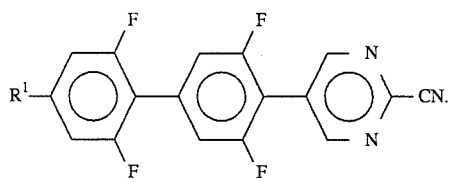

$R^1$ is preferably alkyl, alkoxy, oxaalkylyl, alkenyl or alkenyloxy having 2–10 C atoms.

If $R^1$ is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkenyl radical, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6-, or -7-enyl, non-1-, -2-, -3-, -4-, -5-, -6-, -7- or -8-enyl, or dec-1-, -2-, -3-, -4-, -5-, -6-, -7-, -8- or -9-enyl.

Compounds of the formula I containing branched wing groups $R^1$ may occasionally be of importance owing to better solubility in conventional liquid-crystalline base materials, but in particular as chiral dopants if they are optically active.

Compounds of the formula I having $S_A$ phases are suitable, for example, for thermally addressed displays.

Branched groups of this type generally contain not more than one chain branch. Preferred branched radicals Y are isopropyl, 2-butyl (=1-methylpropyl), isobutyl (=2-methylpropyl), 2-methylbutyl, isopentyl (=3-methylbutyl), 2-methylpentyl, 3- methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and of the subformulae, preference is given to those in which at least one of the radicals present therein has one of the preferred meanings given.

The compounds of the formula I are prepared by methods known per se as described in the literature (for example in the standard works, such as Houben-Weyl, Methoden der Organischen Chemie, Georg-Thieme-Verlag, Stuttgart, Vol. IX, pp. 867 ff.), to be precise under reaction conditions which are known and suitable for said reactions. Use may also be made here of variants which are known per se, but are not described here in greater detail.

The compounds according to the invention can be prepared, for example, by metallating a compound of the formula II

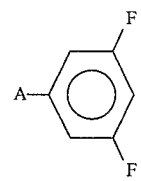

in which A- is a radical of the formula

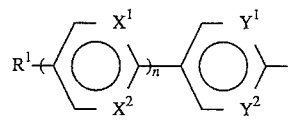

in accordance with the following reaction scheme, and subsequently reacting the product with a suitable electrophile:

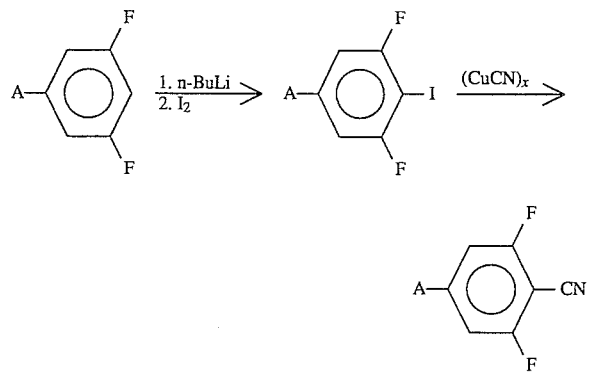

Further synthetic methods are evident to a person skilled in the art. For example, 1,3-difluorobenzene compounds which are appropriately substituted in the 5-position can be converted into the 2-cyano-1,3-difluoro compound in accordance with the above scheme, and the radical A- can subsequently be introduced by reactions customary in liquid-crystal chemistry (for example couplings, for example as in the article by E. Poetsch, Kontakte (Darmstadt) 1988 (2), p. 25).

The compounds of the formula II can be prepared, for example, by the following synthetic schemes:

Scheme 1
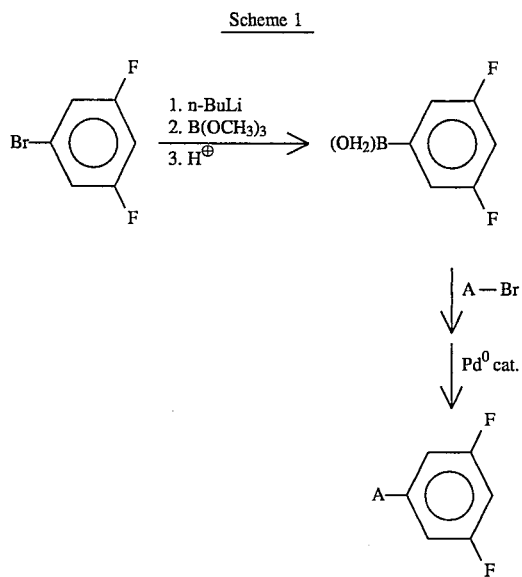
Scheme 2
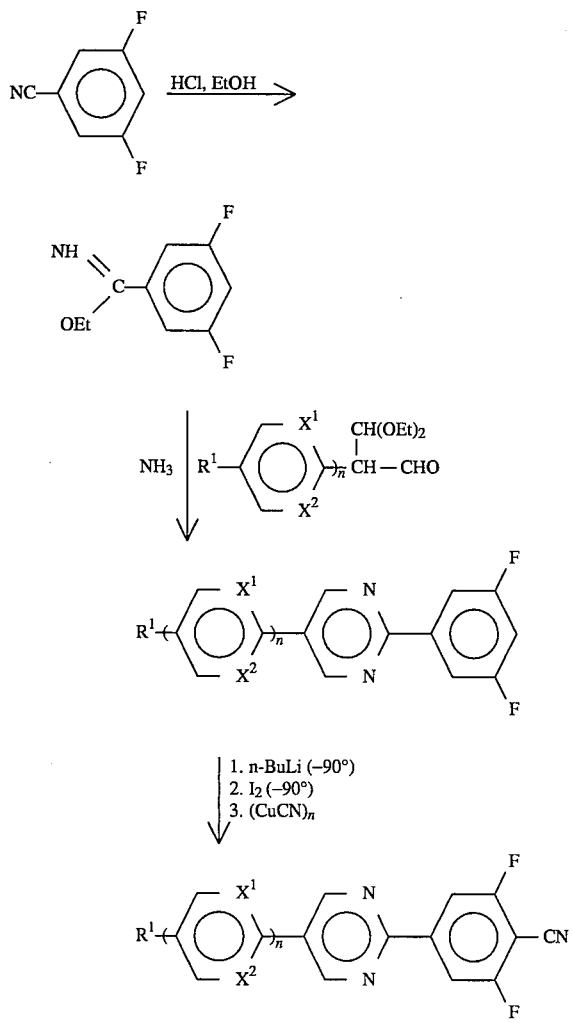
Scheme 3
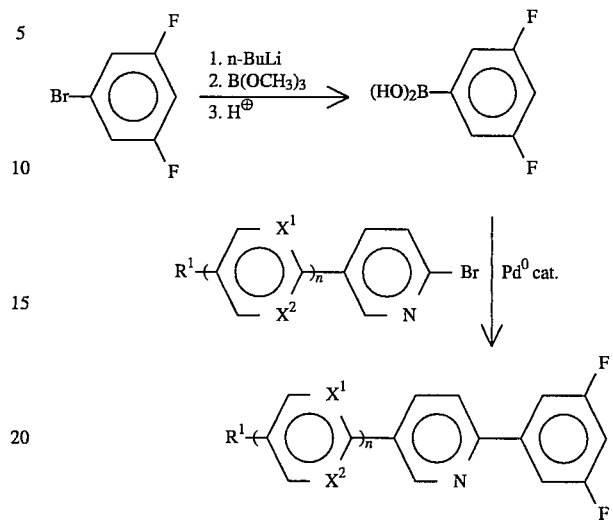
Scheme 4
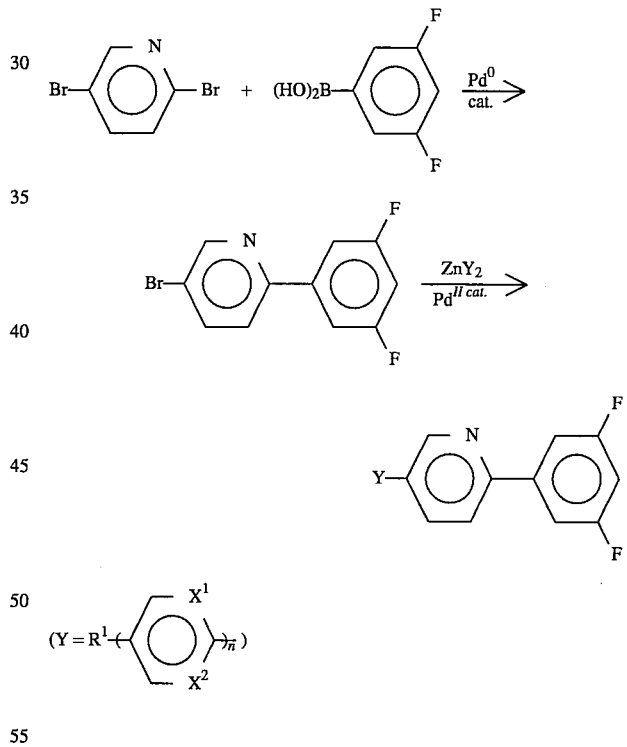
Scheme 5
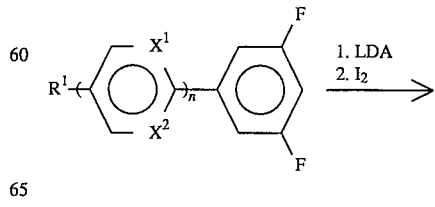

-continued
Scheme 5

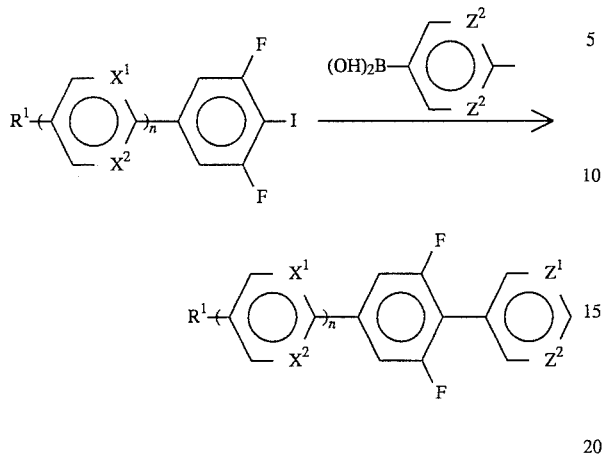

-continued
Scheme 8

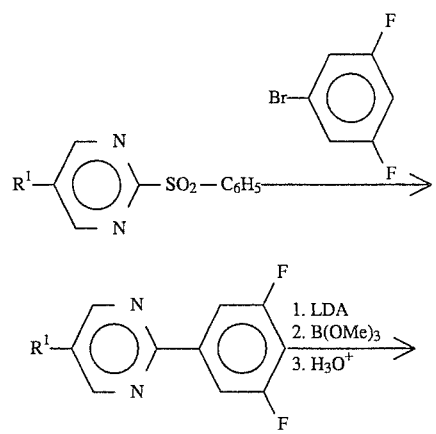

Scheme 6

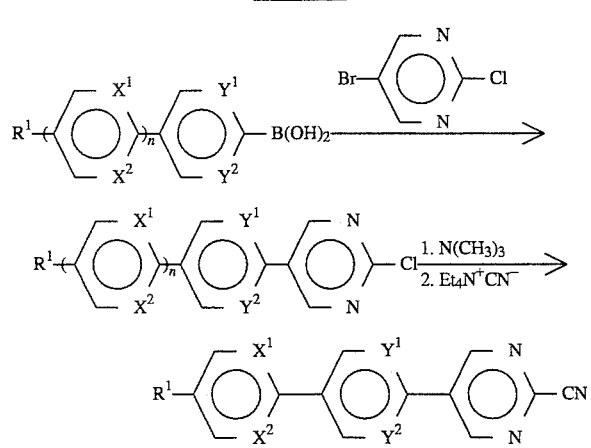

The starting materials are either known or can be prepared analogously to known compounds.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl Scheme 7

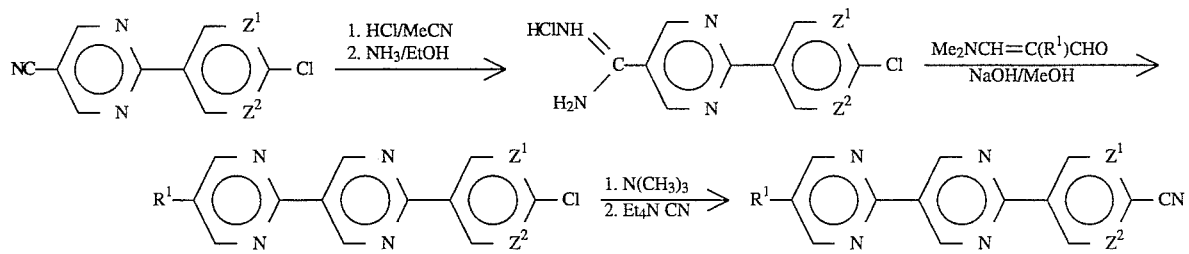

Scheme 8

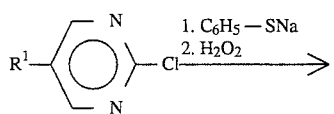

esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

R'—L—E—R"  1

R'—L—COO—E—R"  2

R'—L—OOC—E—R"  3

R'—L—CH$_2$CH$_2$,E—R"  4

R'—L—C≡C—E—R"  5

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In the compounds of the subformulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the subformulae 1b, 2b, 3b, 4b and 5b, R" is -CN, -CF$_3$, F, Cl or -NCS; in this case, R has the meaning given for the compounds of the subformulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group consisting of the compounds 1a, 2a, 3a, 4a and 5a (Group 1), the media according to the invention preferably also contain components from the group consisting of the compounds 1b, 2b, 3b, 4b and 5b (Group 2), whose proportions are preferably as follows:

Group 1: 20 to 90%, in particular 30 to 90%,

Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the examples, m.p.=melting point, c.p.–clearing point. In addition, C=crystalline state, N=nematic phase, S=smectic phase and I=isotropic phase. The numbers between these symbols indicate the conversion temperatures in degrees Celsius. An denotes optical anisotropy (589 nm, 20° C.), and the viscosity (mm$^2$/sec) was determined at 20° C.

"Customary work-up" means that water is added, the mixture is extracted with methylene chloride, diethyl ether or toluene, the organic phase is separated off, dried and evaporated, and the product is purified by distillation under reduced pressure, crystallization and/or chromatography. The following abbreviations are used:

n-BuLi n-butyllithium

DAST diethylaminosulfur trifluoride

DCC dicyclohexylcarbodiimide

DDQ dichlorodicyanobenzoquinone

DIBALH diisobutylaluminum hydride

DMSO dimethyl sulfoxide

POT potassium tertiary-butoxide

THF tetrahydrofuran pTSOH p-toluenesulfonic acid

TMEDA tetramethylethylenediamine

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 43 11 098.3, filed Apr. 3, 1993, are hereby incorporated by reference.

EXAMPLE 1

1A 5-(4-pentyl-2,6-difluorophenyl)-2-chloropyrimidine

A mixture of 0.22 mol of 4-pentyl-2,6-difluorophenylboronic acid (prepared from 5-pentyl-1,3-difluorobenzene and trimethyl borate using n-butyllithium), 0.18 mol of 5-bromo-2-chloropyrimidine, 550 ml of THF, 75 ml of an aqueous buffer solution (pH=8), 230 ml of an aqueous disodium tetraborate decahydrate solution (4%), 200 ml of water and 2 g of tetrakis[triphenylphosphine]palladium (0) is heated at the boil for 20 hours. Customary work-up gives the product, which can be further processed without purification.

1B 5-(4-pentyl-2,6-difluorophenyl)-2-(3,5-difluorophenyl)pyrimidine

A mixture of 77 mmol of 1A, 92 mmol of 3,5-difluorophenylboronic acid (prepared from 3,5-difluorobromobenzene by reaction with magnesium and trimethyl borate), 200 ml of toluene, 92 ml of ethanol, 2.4 g of tetrakis[triphenylphosphine]palladium(0) and 125 ml of a 2 molar aqueous sodium carbonate solution is heated at the boil for 16 hours. Customary work-up gives the product, which can be processed further without purification.

1C 4-[5-(4-pentyl-2,6-difluorophenyl)-pyrimidin-2-yl]-2,6-difluorobenzonitrile

A mixture of 44 mmol of 1B and 80 ml of THF is added dropwise at −78° C. to a solution of 48 mmol of lithium diisopropylamide in hexane. The mixture is stirred at −50° C. for 2 hours and then re-cooled to −78° C., and a mixture of 48 mmol of p-toluenesulphonyl cyanide in 20 ml of THF is slowly added dropwise. After warming to room temperature and conventional work-up, the pure product is obtained by recrystallization from ethanol. C 85 N (75) I, Δε=71.3, Δn=0.232 (extrapolated from ZLI-4792)

EXAMPLES 2 to 22

The following compounds according to the invention are obtained analogously from the corresponding precursors.

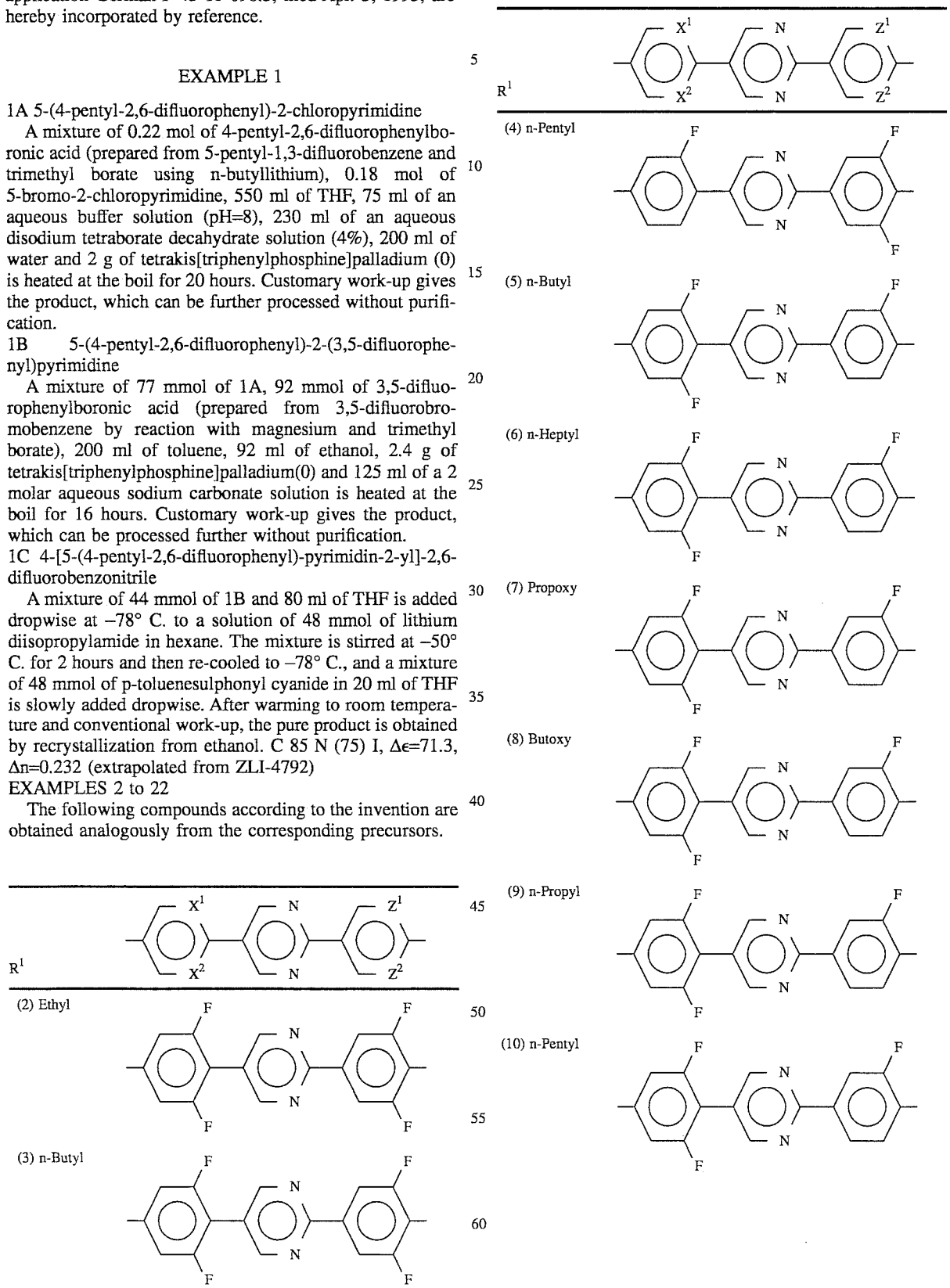

-continued

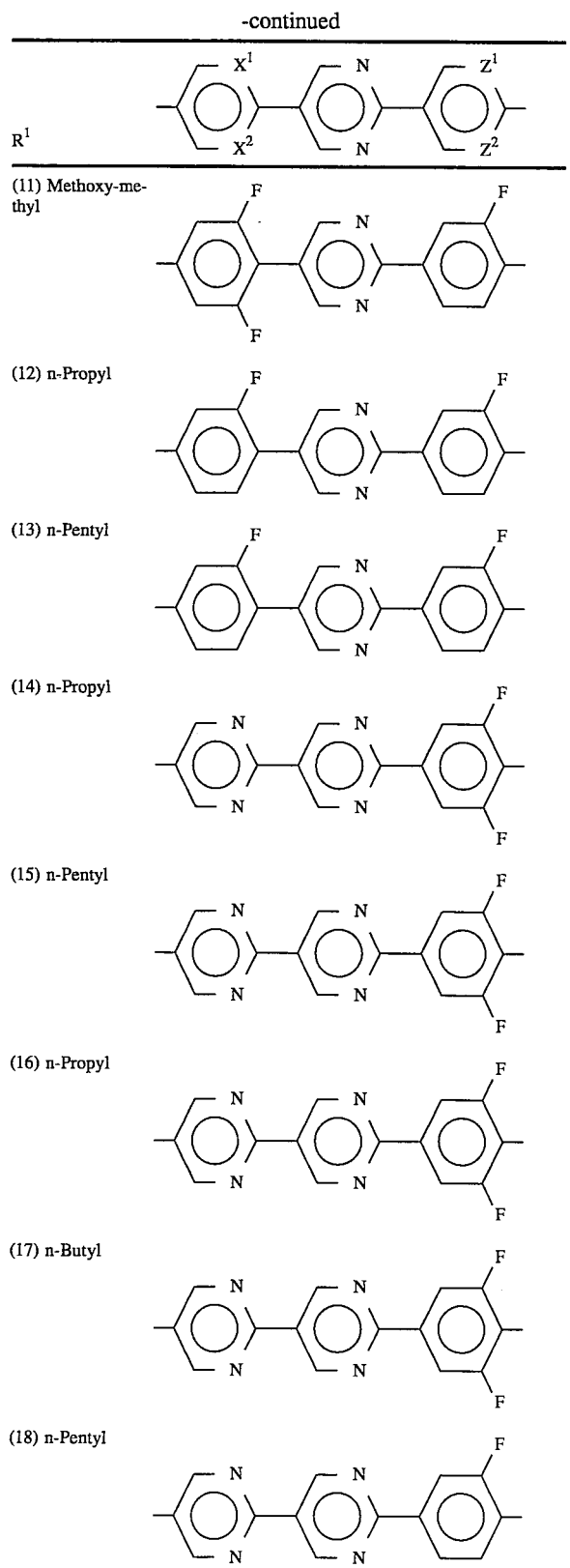

| R¹ | structure |
|---|---|
| (11) Methoxy-methyl | |
| (12) n-Propyl | |
| (13) n-Pentyl | |
| (14) n-Propyl | |
| (15) n-Pentyl | |
| (16) n-Propyl | |
| (17) n-Butyl | |
| (18) n-Pentyl | |

-continued

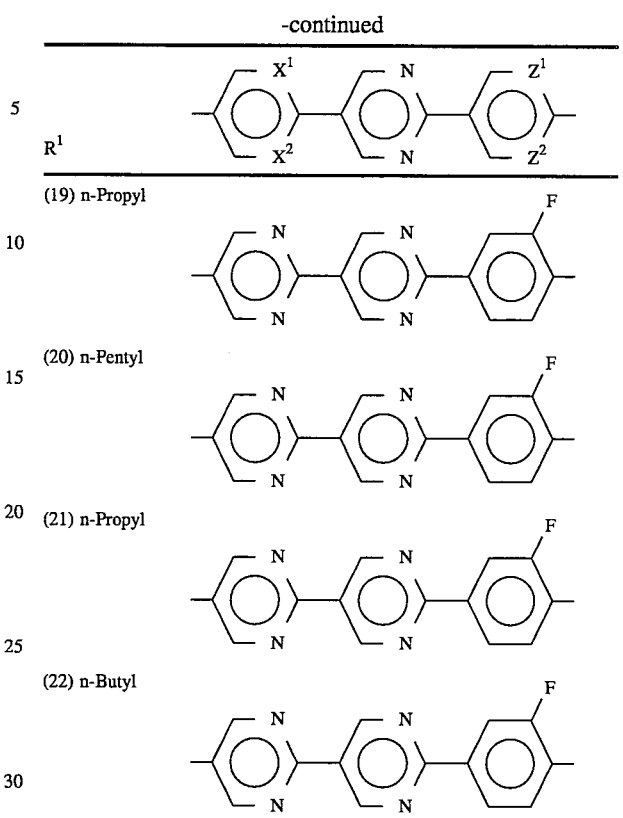

| R¹ | structure |
|---|---|
| (19) n-Propyl | |
| (20) n-Pentyl | |
| (21) n-Propyl | |
| (22) n-Butyl | |

EXAMPLE 23

23A 2-(3,5-difluorophenyl)-5-pentylpyrimidine 80 mmol of 3,5-difluorophenylboronic acid are coupled to 80 mmol of 5-pentyl-2-chloropyrimidine analogously to Example IB 23B 2-(3,5-difluoro-4-iodophenyl)-5-pentylpyrimidine A mixture of 28 mmol of 23A and 110 ml of THF is added at −78° C. to a solution of 17.5 ml of a lithium diisopropylamide solution (34 mmol).

After the mixture has been stirred for two hours, a mixture of 41 mmol of iodine and 20 ml of THF are slowly added dropwise.

Conventional work-up gives the product, which is processed further without purification. 23C 4-(5-pentylpyrimidin-2-yl)-1,6,3',5'-tetrafluorobiphenyl 35 mmol of 23B are coupled to 3,5-difluorophenylboronic acid analogously to Example 1B.

Conventional work-up gives the product, which is processed further without purification.

23D 4-(5-pentylpyrimidin-2-yl)-1,6,3',5'-tetrafluoro-4'-cyanobiphenyl 16 mmol of 23C are reacted with 18 mmol of p-toluenesulphonyl cyanide analogously to Example 1C. The pure product is obtained after recrystallization from ethanol C 71 N 91 I, Δε=70.5, Δn=0.230 (extrapolated from ZLI-4792)

EXAMPLES 24 to 38
The following compounds according to the invention are obtained analogously from the corresponding precursors
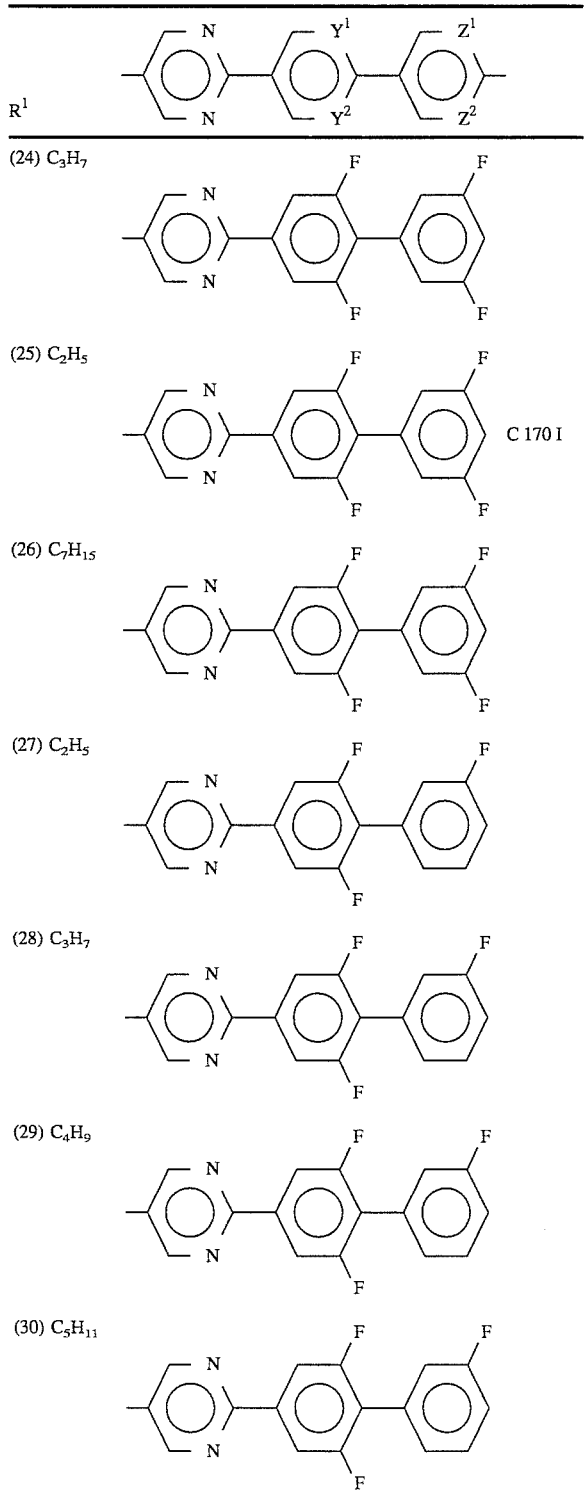
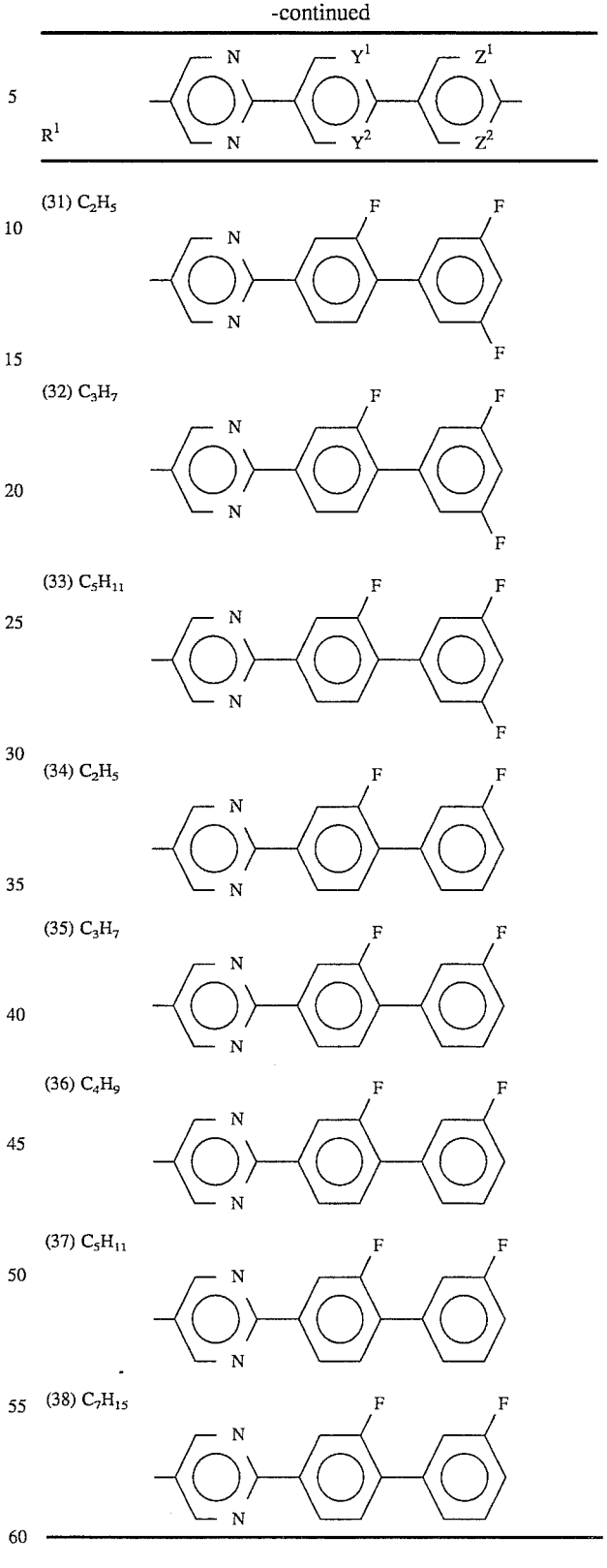

EXAMPLE 39

39A 4'-propyl-2',6',3,5-tetrafluorobiphenyl-4-yl boronic acid 0.6 mol of lithium diisopropylamide is added at 0° C. to a mixture of 0.5 mol of 4'-propyl-2',6',3,5-tetrafluorobiphenyl (prepared from 4-propyl-2,6-difluoroiodobenzene and 3,5-difluorophenylboronic acid analogously to Example 23C). 0.5 mol of trimethyl borate and 500 ml of THF, and the mixture is stirred for two hours.

Acidification and conventional work-up gives the product, which is processed further without purification.

39B 5-(4'-propyl-2',6',3,5-tetrafluorobiphenyl-4-yl)-2-chloropyrimidine 0.25 mol of 39A is coupled to 0.29 mol of 2-chloro-5-bromopyrimidine analogously to Example 1A. The product obtained in this way is processed further without purification.

39C [5-(4'-propyl-2',6',3,5-tetrafluorobiphenyl-4-yl)pyrimidin-2-yl]trimemthylammonium chloride Trimethylamine (0.15 mol) is passed at 45° C. into a mixture of 0.09 mol of 39B and 150 ml of toluene. After the mixture has been stirred at room temperature for 60 hours, the salts formed are separated off, washed a number of times with diethyl ether and dried.

39D 5-(4'-propyl-2',6',3,5-tetrafluorobiphenyl-4-yl)-2-cyanopyrimidine

A mixture of 0.0625 mol of tetraethylammonium cyanide and 100 ml of dichloromethane is added dropwise at room temperature to a mixture of 0.05 mol of 39C and 100 ml of dichloromethane.

After the mixture has been stirred at room temperature for 4 hours, it is subjected to customary work-up. Recrystallization from hexane gives the pure product.

EXAMPLES 40 to 66

The following compounds according to the invention are obtained analogously from the corresponding precursors:

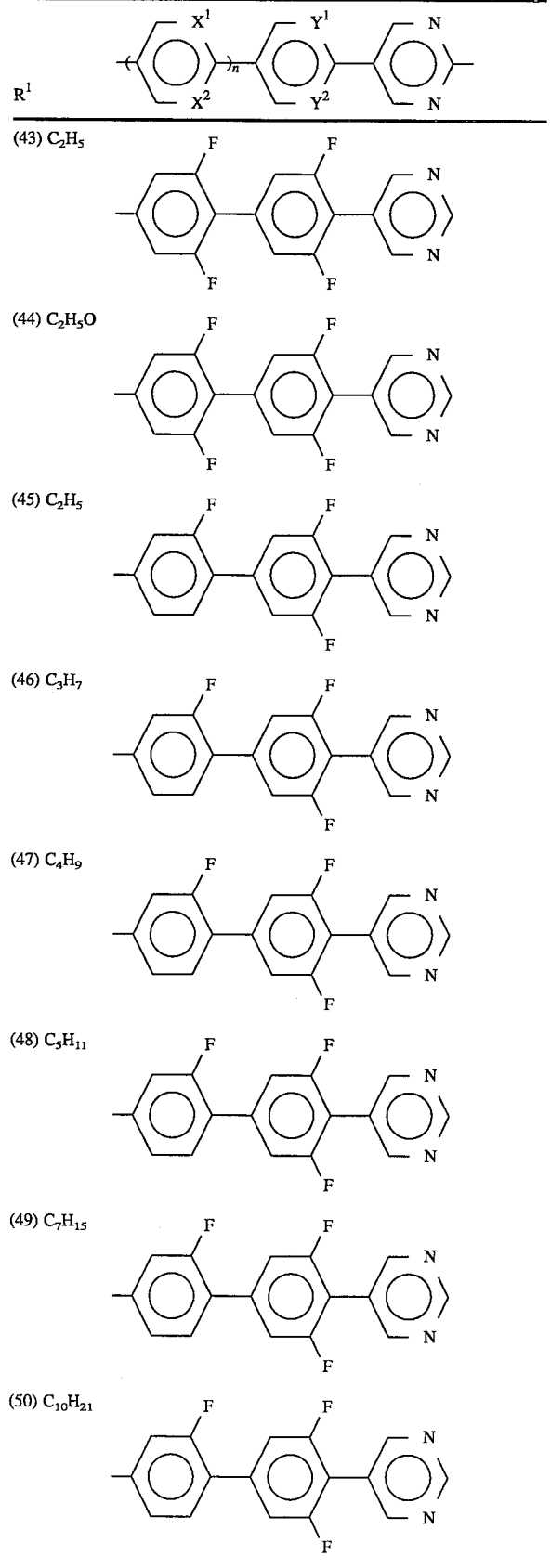

-continued
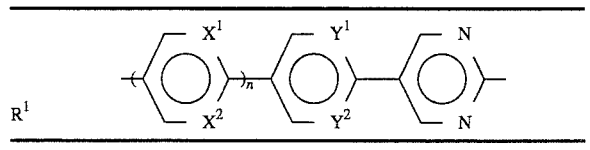
| R¹ | |
|---|---|
| (51) C₄H₉O | 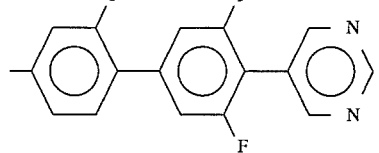 |
| (52) C₂H₅ | 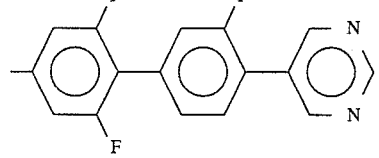 |
| (53) C₃H₇ | 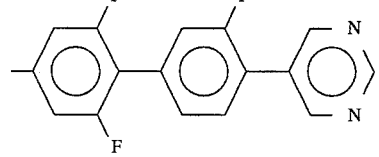 |
| (54) C₄H₉ | 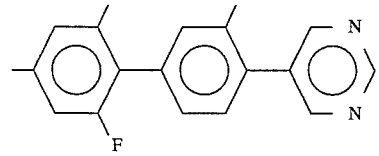 |
| (55) C₅H₁₁ | 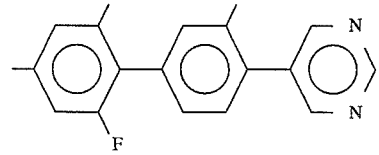 |
| (56) C₂H₅O | 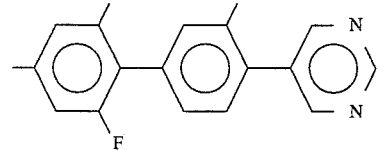 |
| (57) CH₃O | 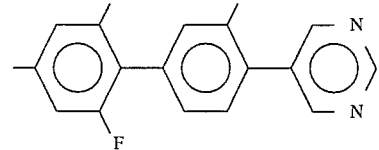 |
| (58) C₂H₅ | 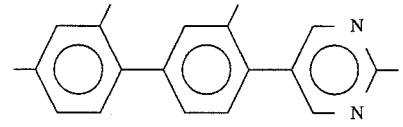 |
-continued
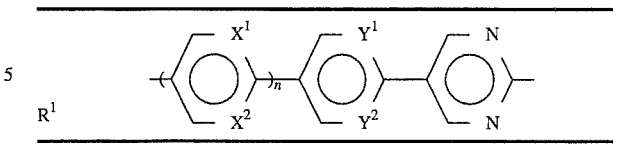
| R¹ | |
|---|---|
| (59) C₃H₇ | 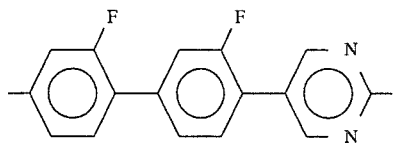 |
| (60) C₅H₁₁ | 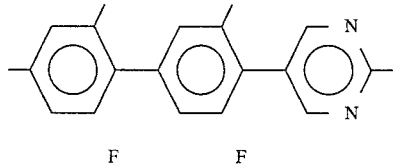 |
| (61) C₂H₅O | 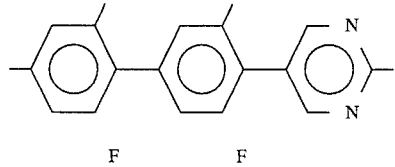 |
| (62) CH₃O | 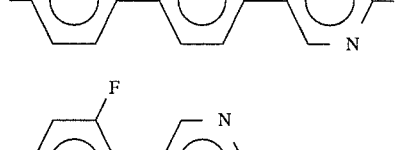 |
| (63) C₂H₅ | 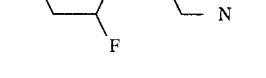 |
| (64) C₃H₇ | 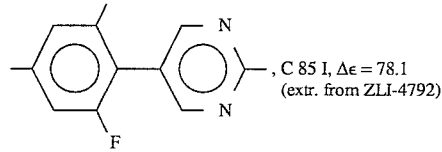, C 85 I, Δε = 78.1 (extr. from ZLI-4792) |
| (65) C₅H₁₁ | 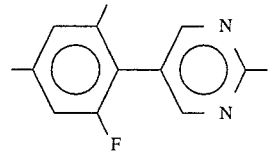 |
| (66) CH₃O | 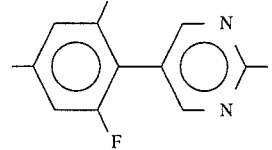 |

Example A

An STN display having a layer thickness of 6 μm, a multiplex rate of 240 and a bias of 16 contains a liquid-crystalline medium having the following properties:

S→N ←−15° C.
N→I +89° C.
Δn 0.1410
HTP −10.2 which comprises an achiral base material comprising:

25.0% of p-(trans-4-propylcyclohexyl)benzonitrile
4.0% of p-(trans-4-butylcyclohexyl)benzonitrile
4.0% of p-[trans-4-(trans-4-ethylcyclohexyl)cyclohexyl] trifluoromethoxybenzene
5.0% of p-[trans-4-(trans-4-propylcyclohexyl)cyclohexyl] trifluoromethoxybenzene
10.0% of p-(trans-4-propylcyclohexyl)methoxybenzene
6.0% of 4-(trans-4-propylcyclohexyl)-4'-methoxytolan
6.0% of 4-(trans-4-propylcyclohexyl)-4'-ethoxytolan
9.0% of trans-4-(trans-4-propylcyclohexyl)ethylcyclohexane
9.0% of trans-4-(trans-4-propylcyclohexyl)butylcyclohexane
2.0% of 4-ethoxy-4'-fluorotolan
6.0% of 4-(trans-4-propylcyclohexyl)-4'-methoxybiphenyl
6.0% of 4-(trans-4-propylcyclohexyl)-4'-ethoxybiphenyl
8.0% of 2-(4-cyano-2,5,2'-6'-tetrafluorobiphenyl-4'-yl)-5-pentylpyrimidine (Example 23)

and a chiral dopant

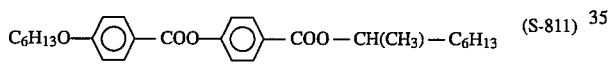

has the following switching behavior:

$V_{10}$: 1.82 V (threshold voltage)
$V_{90}/V_{10}$: 1.080 (steepness of the characteristic line)
Average response time: 205 ms (Arithmetic mean of switch-on and switch-off times).

Example B

An STN display as in Example A contains a liquid-crystalline medium having the following properties:

S→N ←−15° C.
N→I +89° C.
Δn 0.1413
HTP −10.0 which comprises an achiral base material comprising:

22.0% of p-(trans-4-propylcyclohexyl)benzonitrile
3.0% of p-(trans-4-butylcyclohexyl)benzonitrile
5.0% of p-[trans-4-(trans-4-ethylcyclohexyl)cyclohexyl] trifluoromethoxybenzene
5.0% of p-[trans-4-(trans-4-propylcyclohexyl)cyclohexyl] trifluoromethoxybenzene
10.0% of p-(trans-4-propylcyclohexyl)methoxybenzene
5.0% of 4-(trans-4-propylcyclohexyl)-4'-methoxytolan
6.0% of 4-(trans-4-propylcyclohexyl)-4'-ethoxytolan
9.0% of trans-4-(trans-4-propylcyclohexyl)ethylcyclohexane
10.0% of trans-4-(trans-4-propylcyclohexyl)butylcyclohexane
3.0% of 4-ethoxy-4'-fluorotolan
6.0% of 4-(trans-4-propylcyclohexyl)-4'-methoxybiphenyl
6.0% of 4-(trans-4-propylcyclohexyl)-4'-ethoxybiphenyl
10.0% of 2-(4-cyano-2,5,2',6'-tetrafluorobiphenyl-4'-yl)-5-pentylpyrimidine and S-811 has the following switching behavior:

$V_{10}$: 1.74 V
$V_{90}/V_{10}$: 1.080
Average response time: 199 ms

Example C

An STN display as in Example A contains a liquid-crystalline medium having the following properties:

S→N ←−15° C.
N→I +87° C.
Δn 0.1410
HTP −10.35 which comprises an achiral base material comprising:

22.0% of p-(trans-4-propylcyclohexyl)benzonitrile
3.0% of p-(trans-4-butylcyclohexyl)benzonitrile
5.0% of p-[trans-4-(trans-4-ethylcyclohexyl)cyclohexyl] trifluoromethoxybenzene
5.0% of p-[trans-4-(trans-4-propylcyclohexyl)cyclohexyl] trifluoromethoxybenzene
10.0% of p-(trans-4-propylcyclohexyl)methoxybenzene
5.0% of 4-(trans-4-propylcyclohexyl)-4'-methoxytolan
6.0% of 4-(trans-4-propylcyclohexyl)-4-ethoxytolan
9.0% of trans-4-(trans-4-propylcyclohexyl)ethylcyclohexane
10.0% of trans-4-(trans-4-propylcyclohexyl)butylcyclohexane
3.0% of 4-ethoxy-4'-fluorotolan
6.0% of 4-(trans-4-propylcyclohexyl)-4'-methoxybiphenyl
6.0% of 4-(trans-4-propylcyclohexyl)-4'-ethoxybiphenyl
10.0% of 2-(4-cyano-3,5-difluorophenyl)-5-(2,6-difluoro4-pentylphenyl)pyrimidine (Example 1)

and S-811 has the following switching behavior:

$V_{10}$: 1.71 V
$V_{90}/V_{10}$: 1.076
Average response time: 224 ms

Comparative Example

An STN display as in Example A contains a liquid-crystalline medium having the following properties:

S→N ←−15° C.
N→I +80° C.
Δn 0.1400
HTP −10.1 which comprises an achiral base material comprising:

22.0% of p-(trans-4-propylcyclohexyl)benzonitrile
6.0% of p-(trans-4-butylcyclohexyl)benzonitrile
5.0% of p-[trans-4-(trans-4-ethylcyclohexyl)cyclohexyl]-trifluoromethoxybenzene
5.0% of p-[trans-4-(trans-4-propylcyclohexyl)cyclohexyl] trifluoromethoxybenzene
5.0% of p-[trans-4-butylcyclohexyl)cyclohexyl] trifluoromethoxybenzene 5.0% of p-(trans-4-propylcyclohexyl)-4'-methoxybenzene 6.0% of 4-(trans-4-propylcyclohexyl)-4'-ethoxytolan 5.0% of 4-(trans-4-propylcyclohexyl)-4'-propoxytolan 10.0% of trans-4-(trans-4-propylcyclohexyl)ethylcyclohexane 10.0% of trans-4-(trans-4-propylcyclohexyl)butylcyclohexane 4.0% of 4-ethoxy-4'-fluorotolan 4.0% of 4-(trans-4-propylcyclohexyl)-4'-methoxybipheny 3.0% of 4-(trans-4-propylcyclohexyl)-4'-ethoxybiphenyl 3.0% of 4-cyano-3-fluorophenyl-4-ethylbenzoate 3.0% of 4-cyano-3-fluorophenyl-4-propylbenzoate 3.0% of 4-cyano-3-fluorophenyl-4-pentylbenzoate and S-811 has the following switching behavior:

$V_{10}$: 1.89 V $V_{90}/V_{10}$: 1.060

Average response time: 227 ms

The STN displays according to the invention have low threshold voltages and shorter response times.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cyanophenylpyridine or cyanophenylpyrimidine derivative of the formula I

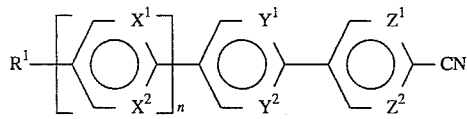

in which $R^1$ is an unsubstituted or at least mono-halogen-substituted alkyl or alkoxy radical having 1 to 15 carbon atoms, in which at least one $CH_2$ group is optionally independently replaced by —CH=CH—, —O—, —S—,

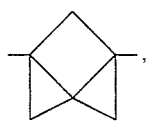

—CO—, —CO—O—, —O—CO— or —O—CO—O— in such a way that oxygen atoms are not linked directly to one another, $X^1$, $Y^1$ and $Z^1$ are each independently N or CF, with at least one of $X^1$, $Y^1$ or $Z^1$ being N, $X^2$, $Y^2$ and $Z^2$ are each independently N or CF, and n is 1 or 2.

2. A cyanophenylpyrimidine derivative according to claim 1 of formula I1

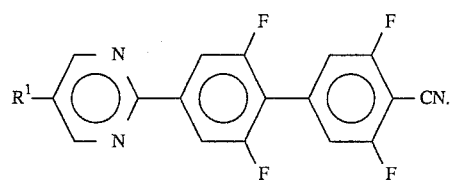

3. A cyanophenylpyrimidine derivative according to claim 1 of formula I2

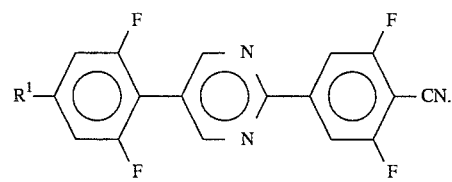

4. A cyanopyrimidine derivative according to claim 1 of formula I3

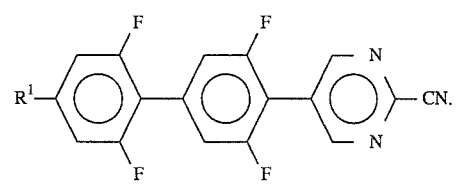

5. A liquid-crystalline medium comprising at least two liquid crystalline components, wherein at least one component is a compound according to claim 1 of formula I

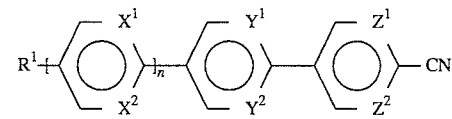

formula I1

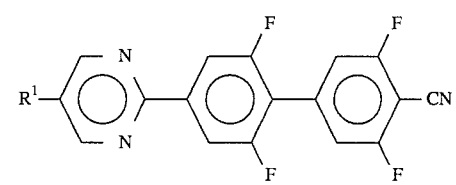

formula I2

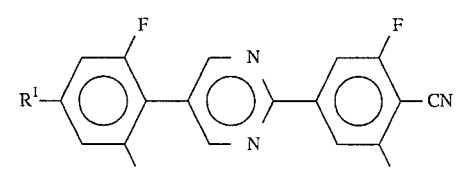

or formula I3

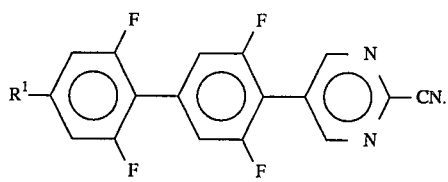
6. An electro-optical component comprising a liquid-crystalline medium according to claim 5.
* * * * *